US012797341B2

(12) United States Patent
Cho et al.

(10) Patent No.: US 12,797,341 B2
(45) Date of Patent: Nov. 17, 2026

(54) PREFILLED PATCH

(71) Applicant: LABNPEOPLE CO., LTD., Gyeonggi-do (KR)

(72) Inventors: Sung Youn Cho, Gyeonggi-do (KR); Yong Kwon Kwak, Gyeonggi-do (KR)

(73) Assignee: LABNPEOPLE CO., LTD., Gyeonggi-Do (KR)

( * ) Notice: Subject to any disclaimer, the term of this patent is extended or adjusted under 35 U.S.C. 154(b) by 263 days.

(21) Appl. No.: 18/702,799

(22) PCT Filed: Oct. 21, 2022

(86) PCT No.: PCT/KR2022/016123
§ 371 (c)(1),
(2) Date: Apr. 19, 2024

(87) PCT Pub. No.: WO2023/068864
PCT Pub. Date: Apr. 27, 2023

(65) Prior Publication Data

US 2024/0408035 A1 Dec. 12, 2024

(30) Foreign Application Priority Data

Oct. 21, 2021 (KR) ........................ 10-2021-0141091
Oct. 20, 2022 (KR) ........................ 10-2022-0135685

(51) Int. Cl.
*A61K 9/70* (2006.01)

(52) U.S. Cl.
CPC .................................. *A61K 9/7038* (2013.01)

(58) Field of Classification Search
CPC .. A61K 9/7038; A61K 9/0021; A61K 9/7084; A61M 37/00; A61M 2037/0023; A61M 37/0015
See application file for complete search history.

(56) References Cited

U.S. PATENT DOCUMENTS

2010/0239353 A1 9/2010 Prax
2012/0220980 A1* 8/2012 Ross ................ A61M 37/0015 604/173
2015/0335870 A1* 11/2015 Quan ................ A61M 37/0015 604/263
2019/0038884 A1 2/2019 Roux et al.
2019/0114815 A1* 4/2019 Erhard .................. G06T 11/008
2023/0067488 A1 3/2023 Roux et al.

FOREIGN PATENT DOCUMENTS

JP 2012228573 A 11/2012
JP 2014147837 A 8/2014
JP 2020192411 A 12/2020
JP 2021142325 A 9/2021
KR 20-0431584 Y1 11/2006
KR 10-0847222 B1 7/2008
(Continued)

*Primary Examiner* — Susan S Su
*Assistant Examiner* — Erin A Kim
(74) *Attorney, Agent, or Firm* — HAUPTMAN HAM, LLP

(57) ABSTRACT

Proposed is a prefilled patch including an adhesive layer configured to be attached to the skin, a capsule which is provided on the adhesive layer and in which active ingredient or a drug is stored, and a handle connected to a discharge hole formed in the capsule, wherein the handle is separated from the capsule by a user to open the discharge hole.

13 Claims, 15 Drawing Sheets

100

(56) References Cited

FOREIGN PATENT DOCUMENTS

| | | | |
|---|---|---|---|
| KR | 10-2015-0028248 | A | 3/2015 |
| KR | 10-1502157 | B1 | 3/2015 |
| KR | 10-1858394 | B1 | 5/2018 |
| KR | 10-2019-0080325 | A | 7/2019 |
| KR | 10-2019-0114815 | A | 10/2019 |
| KR | 10-2020-0076216 | A | 6/2020 |
| KR | 10-2021-0100856 | A | 8/2021 |
| KR | 10-2417441 | B1 | 7/2022 |

* cited by examiner

[FIG. 1]
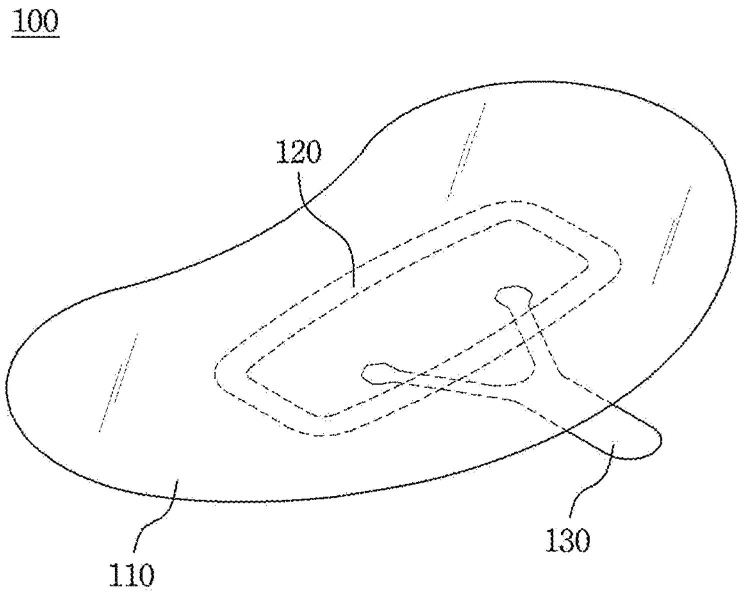

[FIG. 2A]
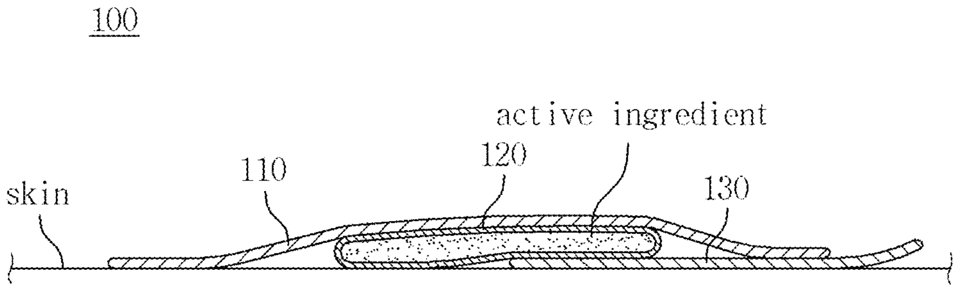
[FIG. 2B]
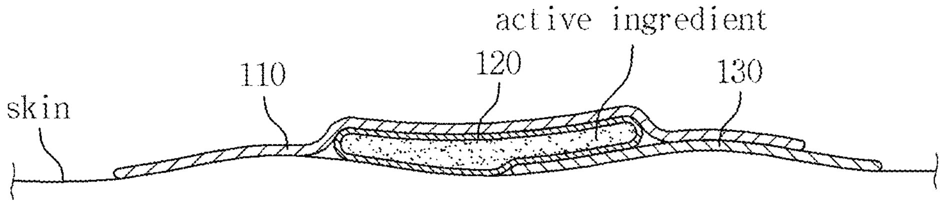
[FIG. 3]
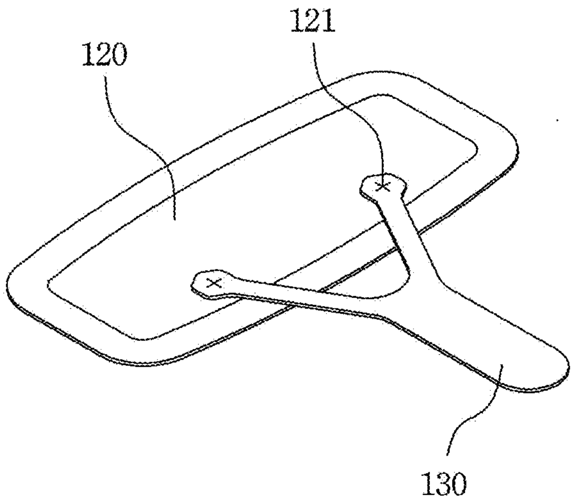

[FIG. 4A]
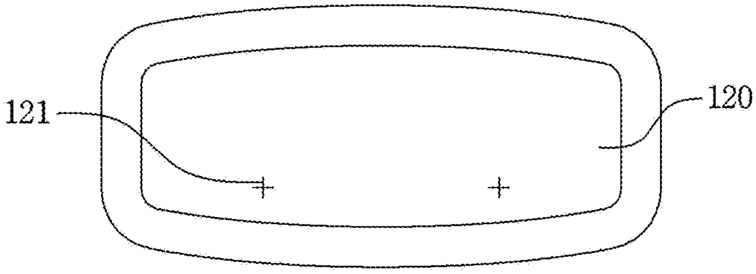
[FIG. 4B]
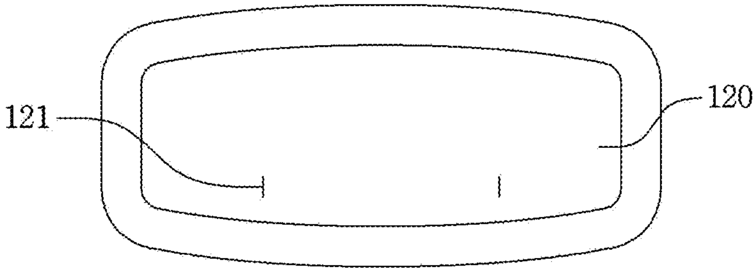
[FIG. 4C]
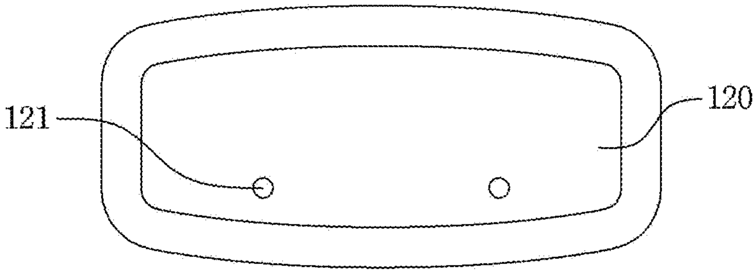

[FIG. 5]
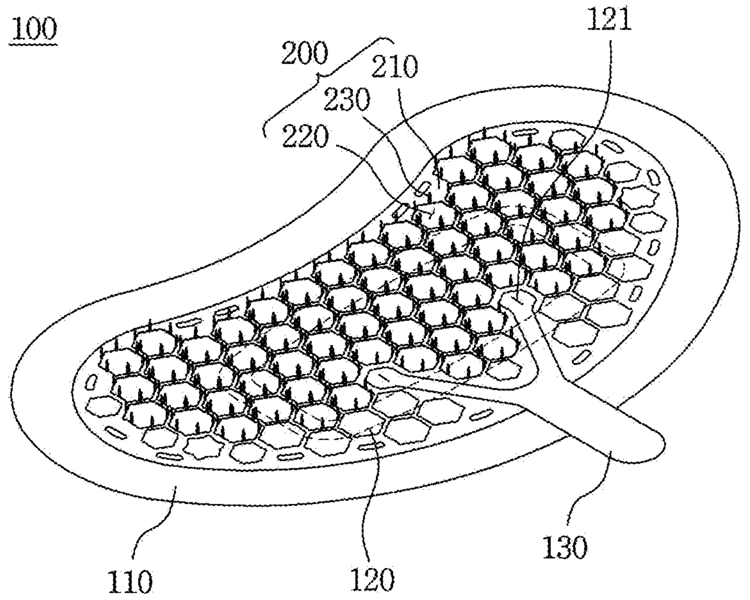

[FIG. 6]
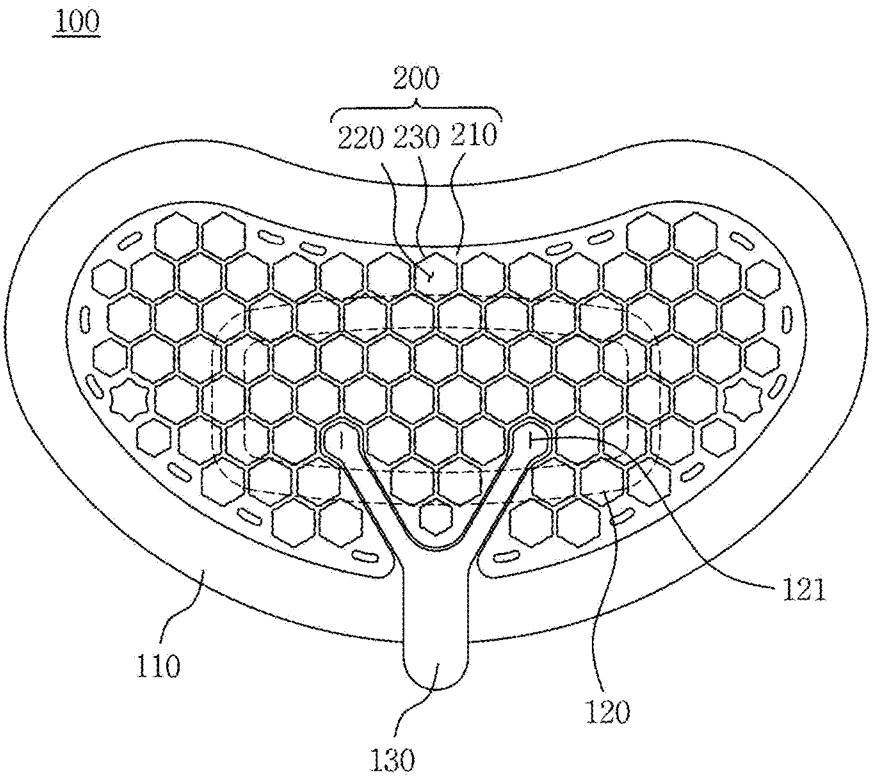

[FIG. 7]
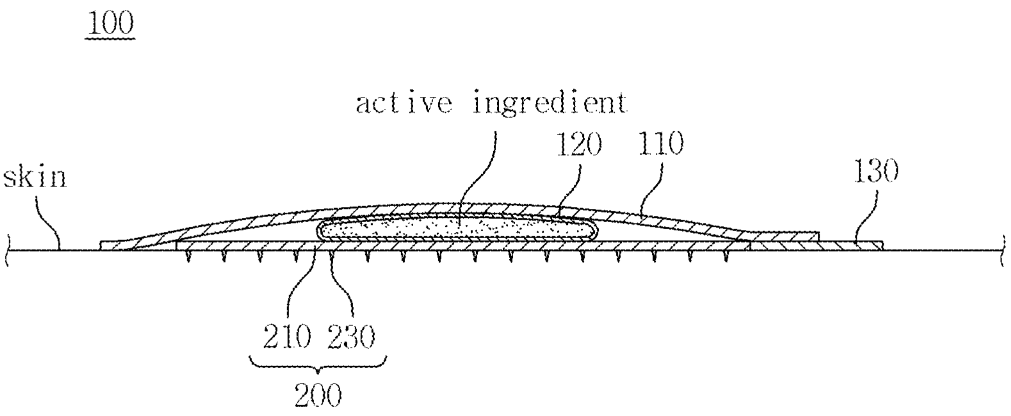
[FIG. 8]
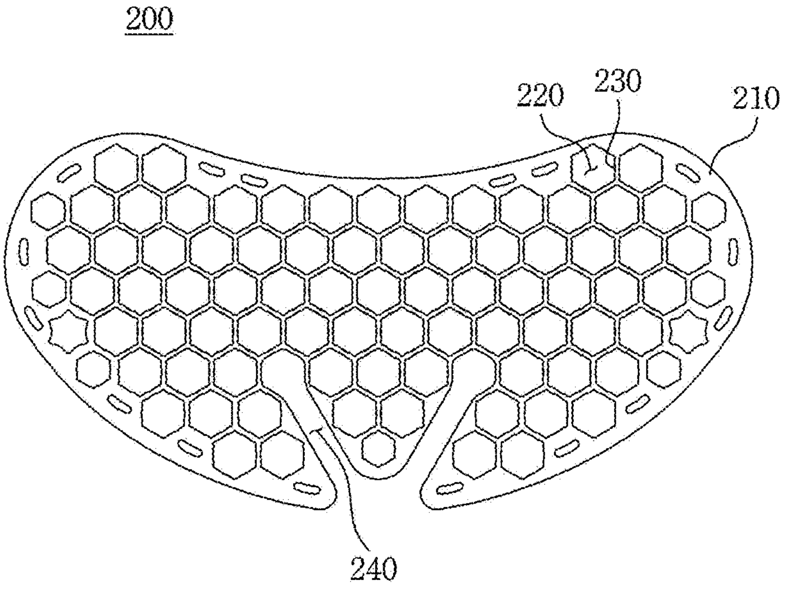

[FIG. 9]
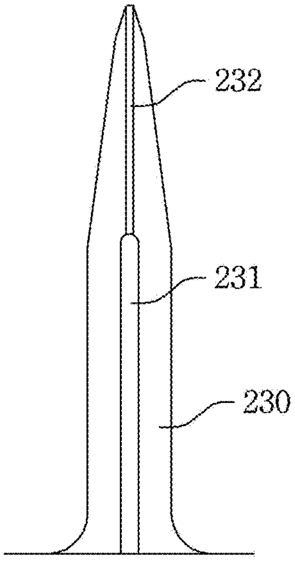

[FIG. 10]
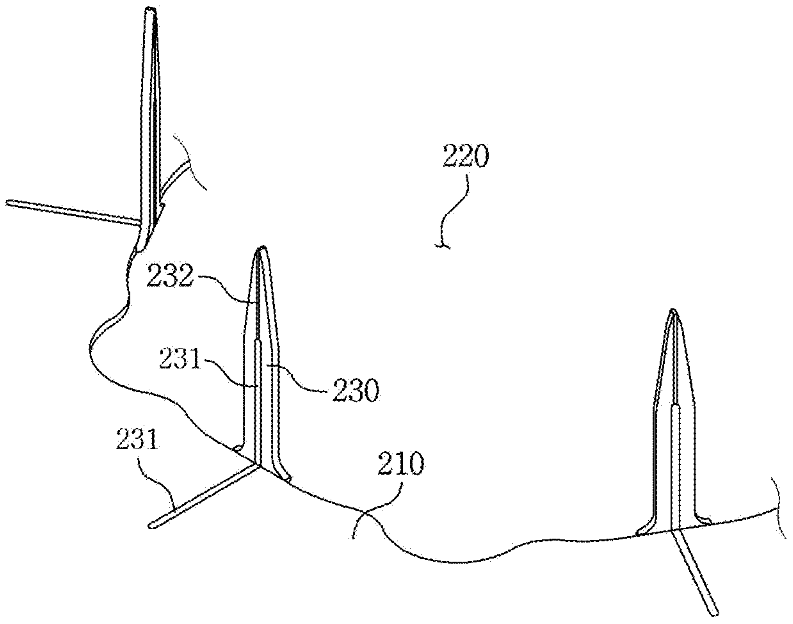

[FIG. 11]
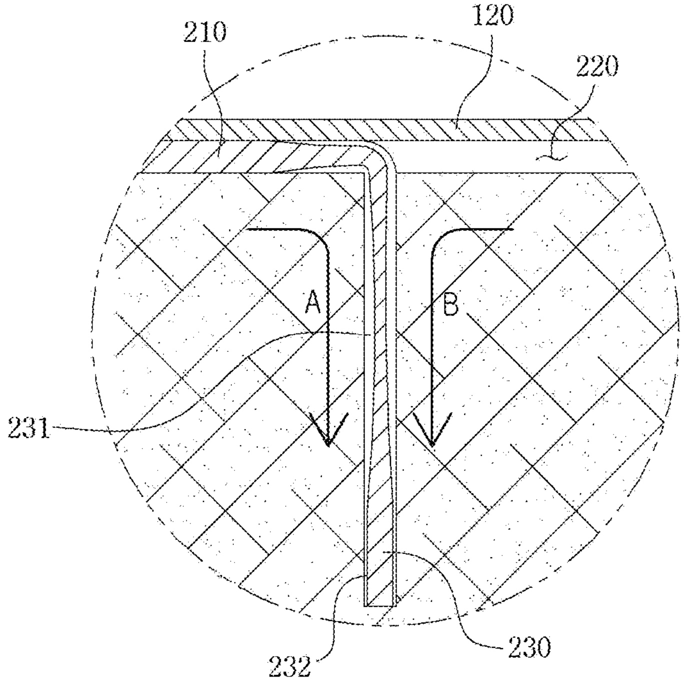

[FIG. 12]

| sample | thickness of adhesive layer (mm) | amount of active ingredient (ml/cm²) | capsule protrusion height (maximum value, mm) | discharge of active ingredient (capsule->skin) | leakage of active ingredient (skin->outside of patch) |
|---|---|---|---|---|---|
| #1 | 0.5 | 0.01 | 0.5 | discharged | leaked |
| #2 | 1 | 0.005 | 0.3 | not discharged | - |
| #3 | 1 | 0.01 | 0.5 | discharged | leaked X |
| #4 | 1 | 1.00 | 10 | discharged | leaked X |
| #5 | 1 | 3.00 | 15 | discharged | leaked |
| #6 | 2 | 1.00 | 10 | discharged | leaked X |
| #7 | 2 | 3.00 | 15 | discharged | leaked |

[FIG. 13]
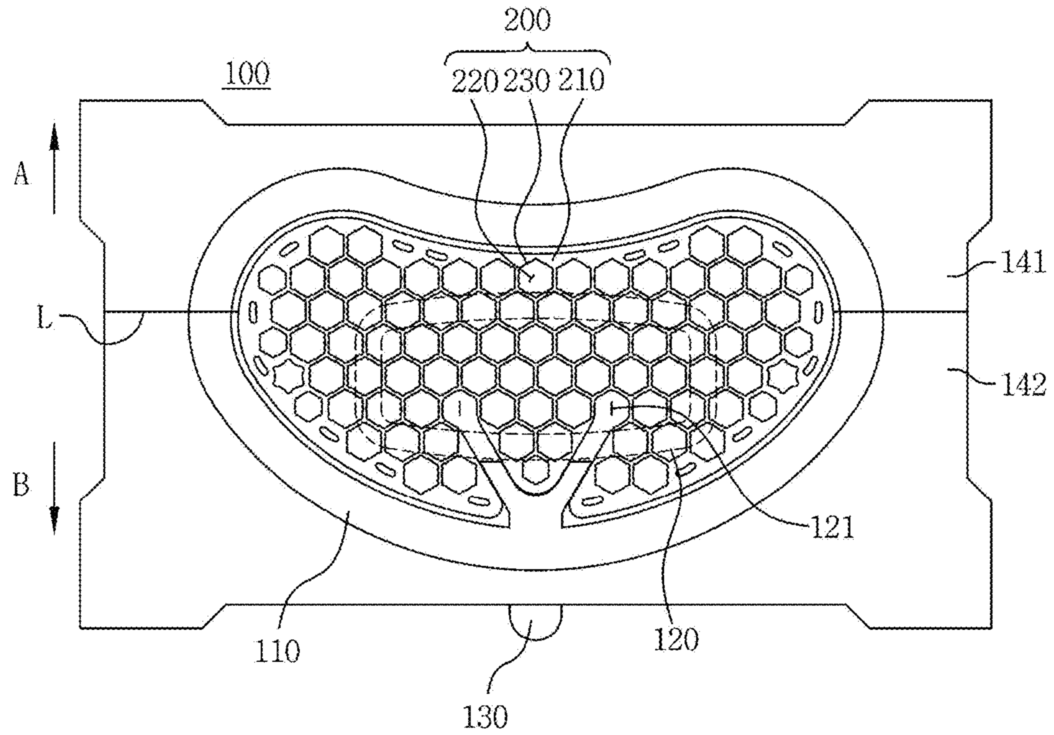

[FIG. 14]
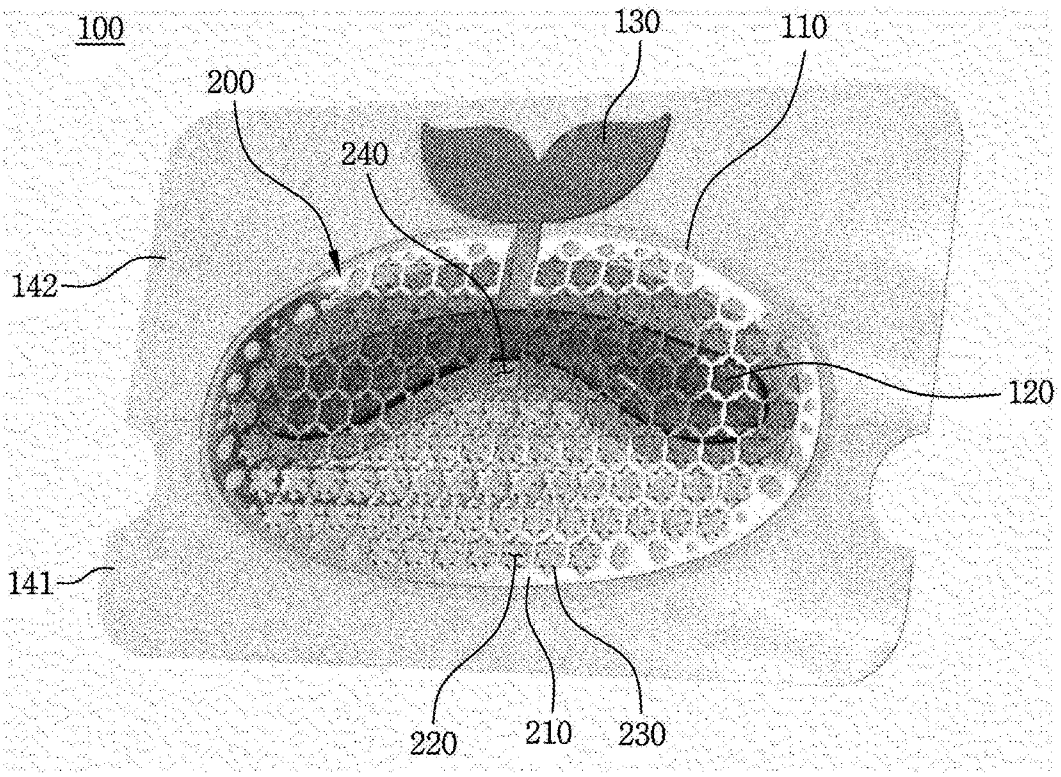

[FIG. 15]
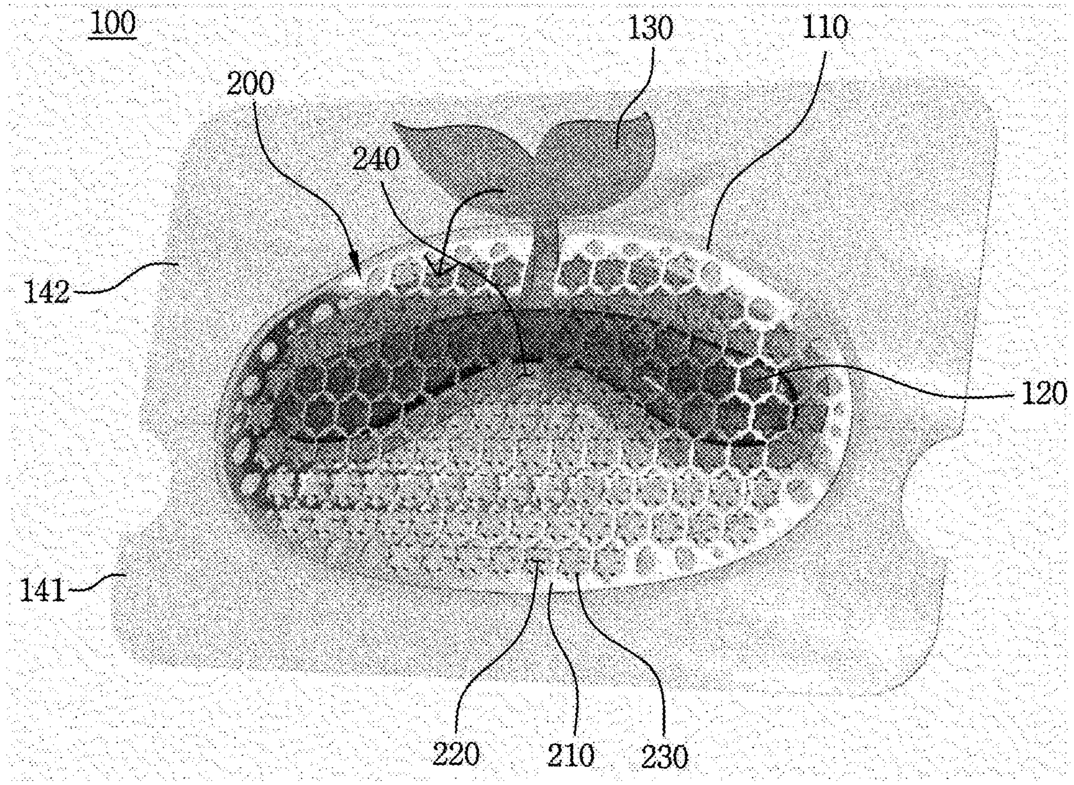

[FIG. 16]
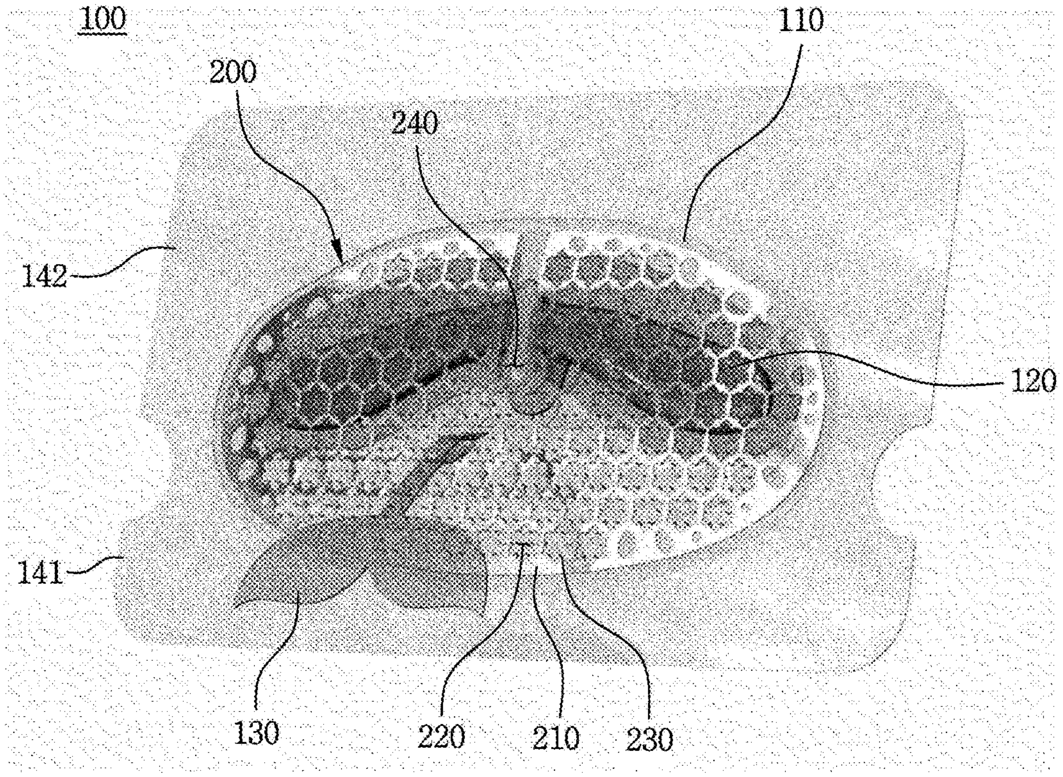

[FIG. 17]
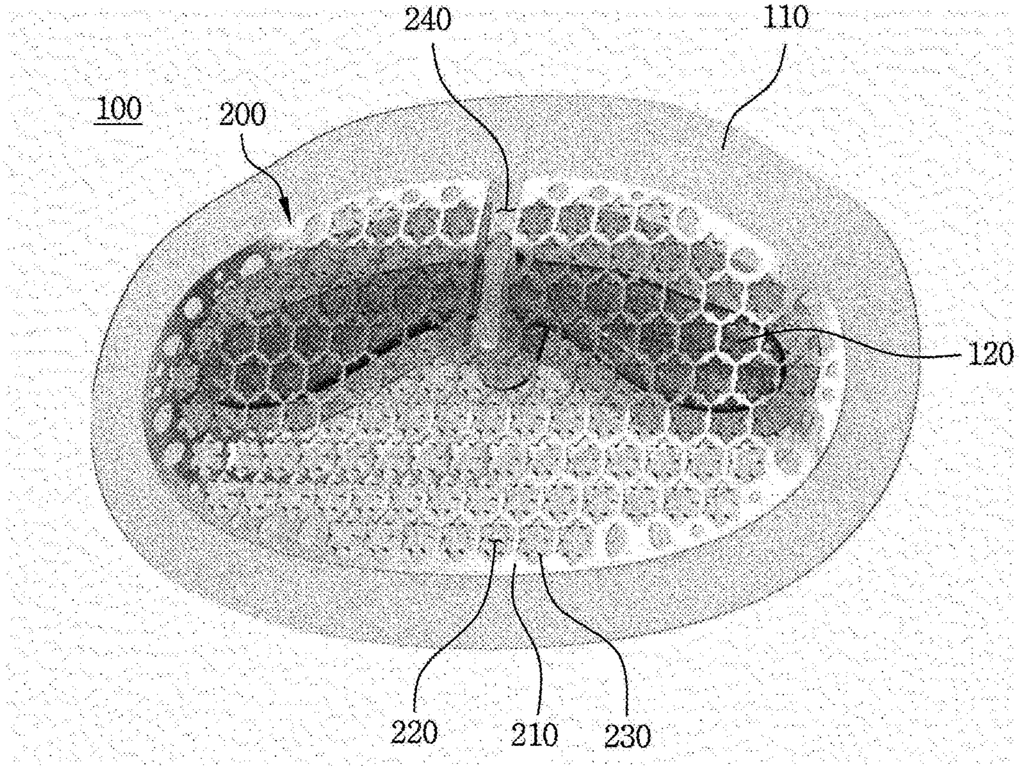

PREFILLED PATCH

RELATED APPLICATIONS

The present application is a National Phase of International Application No. PCT/KR2022/016123, filed Oct. 21, 2022, and claims priority based on Korean Patent Application No. 10-2021-0141091, filed Oct. 21, 2021 and Korean Patent Application No. 10-2022-0135685, filed Oct. 20, 2022.

TECHNICAL FIELD

The present disclosure relates to a prefilled patch attached to the skin to deliver liquid active ingredients or drugs into the body.

BACKGROUND ART

In general, methods for delivering active ingredients or drugs into the body include drug taking (swallowing), drug injection, and drug absorption through the skin.

Among these methods, oral administration, that is, drug taking, may cause central nervous system side effects such as headache, drowsiness, dizziness, and nervousness and serious gastrointestinal side effects such as nausea, indigestion, diarrhea, peptic ulcer, gastrointestinal bleeding, and perforation. Thus, the use of the oral route of administration is limited to short-term treatment.

Drug injection involves inserting a needle through the skin and introducing a drug directly into the body, which allows for rapid absorption, but is inconvenient because a drug needs to be administered by a professional (self-administration is difficult). In addition, since a needle with a diameter of several millimeters is usually used for drug injection, pain experienced by patients may lead to poor patient compliance with treatment.

In order to overcome the above-mentioned side effects and drawbacks, research and development of transdermal drug delivery systems are being actively conducted.

Typically, drugs that are absorbed through the skin are formulated in the form of a liquid, cream, or gel. However, due to the nature of the liquid, cream, and gel formulations, controlling the dosage difficult, and stickiness and staining clothes may also be a problem.

For this reason, a method of attaching a patch containing a drug to the skin and allowing the drug to be absorbed through the skin is used.

Transdermal drug delivery using a patch may prevent side effects such as gastrointestinal disorders caused by taking medication and food interactions from drugs since a drug is absorbed through the skin, and may eliminate pain and discomfort associated with injection, offering a convenient way to administer medication, which results in a gradual increase in the use of transdermal patches recently.

A patch may be largely composed of a drug-impermeable backing layer through which a drug does not pass, a drug-permeable membrane, and an adhesive layer that adheres the patch to the skin, and a storage tube in which the drug is stored is provided between the backing layer and the drug-permeable membrane.

The major disadvantage of a patch is that the rate of drug absorption through the skin is low, making it essential for a permeability barrier function of the skin to be reduced. Generally, the rate of delivery from patches is known to be and strategies to improve the drug approximately 20%, absorption rate known to date include chemical methods such as the use of transdermal absorption accelerators and prodrugs, and physical methods such as iontophoresis and electrophoresis.

However, even if these known methods are used, there is still a limit to improving the drug absorption rate to a satisfactory level. In order to expect drug efficacy, excessive use of a drug is inevitable considering the absorption rate.

In particular, in the case of transdermal absorption accelerators, the type of transdermal absorption accelerator is determined depending on the design type of a drug to be used or the physical and chemical properties of ingredients, and a concentration above a certain level is required to be effective. The problem is that when transdermal absorption accelerators are added, it is not easy to prevent crystal formation over time, and adhesive properties such as adhesion and cohesion change to be unsuitable for use.

Moreover, techniques that use electricity to enhance transdermal drug delivery requires a patch to contain batteries, electrodes, circuits, and other components, making a product more complex, larger in size, and more expensive, and generating a large amount of waste after use.

Accordingly, dissolving polymer microneedles containing active ingredients or drugs have been developed, aiming to increase the skin absorption rate of active ingredients or drugs. However, the disadvantages of soluble microneedles are that they carry a smaller dose of drug-loaded quantity, have low skin penetration efficiency due to insufficient strength of polymers, and tend to break when attached to the skin obliquely rather than vertically. Thus, it is difficult to commercialize dissolving microneedles for medical purposes.

The present applicant has developed the disclosed technology to solve the above problems, and as an example of related art, there is Korean Patent No. 10-0847222 "PHASE TRANSITION COSMETIC TRANSDERMAL DELIVERY SYSTEM WITH INCREASED SKIN ABSORPTION".

DISCLOSURE

Technical Problem

The present disclosure is intended to solve the above problems occurring in the related art. An objective of the present disclosure is to provide a prefilled patch designed to prevent evaporation of liquid active ingredients or drugs, increase the skin absorption rate, and store high doses of active ingredients or drugs.

An objective of the present disclosure is to provide a prefilled patch designed to prevent liquid active ingredients or drugs from leaking to the outside of the patch due to the curvature of the skin when attached to the skin.

An objective of the present disclosure is to provide a prefilled patch designed to allow liquid active ingredients or drugs to quickly penetrate the skin.

An objective of the present disclosure is to provide a prefilled patch designed to allow a user to easily open a capsule containing liquid active ingredients and drugs to release a drug into the skin.

Technical Solution

In order to achieve the above mentioned objectives, there is provided a prefilled patch including: an adhesive layer configured to be attached to skin; a capsule which is provided on the adhesive layer and in which an active ingredient or a drug is stored; and a handle connected to a discharge hole formed in the capsule, wherein the handle may be separated from the capsule by a user to open the discharge hole.

In addition, the capsule may be provided on a surface of the adhesive layer while being disposed closer to the skin than the adhesive layer, and may have a planar area smaller than a planar area formed by the adhesive layer.

In addition, a first longitudinal end of the handle may block the discharge hole formed in the capsule, and a second longitudinal end of the handle may be exposed to outside of the adhesive layer.

In addition, the discharge hole may be provided in plural numbers, and the first end of the handle may be branched into a number corresponding to the number of the discharge hole.

In addition, the prefilled patch may further include: a microneedle provided by being attached to the adhesive layer with a planar area that is larger than the planar area formed by the capsule and smaller than the planar area formed by the adhesive layer.

In addition, the microneedle may include: a substrate portion configured to be attached to the adhesive layer; a plurality of carrying holes formed in the substrate portion; and an insertion needle provided to protrude from a portion of the substrate portion that partitions the carrying holes, and configured to be inserted into the skin.

In addition, the discharge hole formed in the capsule may correspond to any one of the carrying holes.

In addition, the substrate portion may be provided with a guide area that guides a movement of the handle so that the movement is not interfered with when a portion of the handle connected to the capsule is separated from the capsule.

In addition, the microneedle may further include: a carrying groove that provides a path for the active ingredient or the drug discharged through the discharge hole to flow, wherein the carrying groove may be formed extending from a portion of the area formed by the substrate portion toward an end of the insertion needle.

In addition, the microneedle may further include: a slit groove that guides the active ingredient or the drug loaded in the carrying groove to the end of the insertion needle.

In addition, the substrate portion and the insertion needle of the microneedle may be made of a bioresorbable metal, and the bioresorbable metal may contain at least one of magnesium, calcium, zinc, and iron.

In addition, the prefilled patch may further include: a pair of release papers attached to a peripheral area of the adhesive layer, wherein one and the other of the pair of the release papers may be moved in different directions to be separated from the adhesive layer, and one of the release papers may be attached to the handle.

Advantageous Effects

A prefilled patch according to an embodiment of the present disclosure is configured such that a capsule that discharges an active ingredient or a drug from the inside of an adhesive layer attached to the skin, thereby preventing the active ingredient or the drug from evaporating and increasing skin absorption by keeping the active ingredient or the drug in continuous contact with the skin.

Furthermore, a prefilled patch according to an embodiment of the present disclosure is equipped with a microneedle under an adhesive layer and a capsule, thereby easily delivering an active ingredient or a drug stored in the capsule to deeper layers of the skin via the microneedle and stimulating the skin to provide beneficial effects.

Furthermore, a prefilled patch according to an embodiment of the present disclosure is configured to deliver an active ingredient or a drug stored in a carrying hole or an active ingredient or a drug remaining on the surface of a substrate portion to deeper layers of the skin through a carrying groove and a slit groove formed in an insertion needle, allowing the active ingredient or the drug to quickly penetrate into the deeper layers of the skin.

DESCRIPTION OF DRAWINGS

FIG. 1 is a perspective view of a prefilled patch according to an embodiment of the present disclosure;

FIGS. 2A and 2B are cross-sectional views showing the prefilled patch shown in FIG. 1 attached to the skin;

FIG. 3 perspective view showing the coupling relationship between a capsule and a handle according to an embodiment of the present disclosure;

FIGS. 4A, 4B and 4C are bottom views showing various types of discharge holes formed at the bottom of a capsule according to an embodiment of the present disclosure;

FIG. 5 is a perspective view from the bottom of a state in which a microneedle is provided in a prefilled patch according to an embodiment of the present disclosure;

FIG. 6 is a top view of the prefilled patch shown in FIG. 5;

FIG. 7 is a cross-sectional view showing the prefilled patch shown in FIG. 5 attached to the skin;

FIG. 8 is a top view of the microneedle shown in FIG. 5;

FIG. 9 is a view from the front of an insertion needle of a microneedle according to an embodiment of the present disclosure;

FIG. 10 is a perspective view of the insertion needle shown in FIG. 9;

FIG. 11 is a cross-sectional view showing a state in which an insertion needle according to an embodiment of the present disclosure is inserted into the skin;

FIG. 12 is a test result table showing whether an active ingredient is discharged and leaked according to the thickness of an adhesive layer and the amount of the active ingredient;

FIG. 13 is a plan view showing a state in which a release paper is provided on a prefilled patch according to an embodiment of the present disclosure;

FIG. 14 is a perspective view showing a state in which a handle is integrally connected with a capsule according to an embodiment of the present disclosure;

FIG. 15 is a perspective view showing the handle shown in FIG. 14 being pulled in the direction of the arrow;

FIG. 16 is a perspective view showing the handle shown in FIG. 14 completely separated from the capsule; and FIG. 17 is a perspective view showing a state in which the a release paper shown in FIG. 16 has been removed.

MODE FOR INVENTION

The advantages and features of the present disclosure and methods for achieving them will become clear by referring to the embodiments described in detail below in conjunction with the accompanying drawings.

However, the present disclosure is not limited to the embodiments disclosed below and will be implemented in various different forms. The embodiments are provided solely to ensure that the disclosure of the present disclosure is complete and to fully inform those skilled in the art of the scope of the present disclosure. The present disclosure is defined only by the scope of the claims.

Hereinafter, with reference to FIGS. 1 to 16, a prefilled patch according to an embodiment of the present disclosure is described in detail. In describing the present disclosure, detailed descriptions of related well-known functions or configurations are omitted in order to make the gist of the present disclosure unambiguous.

FIG. 1 is a perspective view of a prefilled patch according to an embodiment of the present disclosure; FIGS. 2A and 2B are cross-sectional views showing the prefilled patch shown in FIG. 1 attached to the skin; FIG. 3 is a perspective view showing the coupling relationship between a capsule and a handle according to an embodiment of the present disclosure; FIGS. 4A, 4B and 4C are bottom views showing various types of discharge holes formed at the bottom of a capsule according to an embodiment of the present disclosure; FIG. 5 is a perspective view from the bottom of a state in which microneedle is provided in a prefilled patch according to an embodiment of the present disclosure; FIG. 6 is a top view of the prefilled patch shown in FIG. 5; FIG. 7 is a cross-sectional view showing the prefilled patch shown in FIG. 5 attached to the skin; FIG. 8 is a top view of the microneedle shown in FIG. 5; FIG. 9 is a view from the front of an insertion needle of a microneedle according to an embodiment of the present disclosure; FIG. 10 is a perspective view of the insertion needle shown in FIG. 9; FIG. 11 is a cross-sectional view showing a state in which an insertion needle according to an embodiment of the present disclosure is inserted into the skin; FIG. 12 is a test result table showing whether an active ingredient is discharged and leaked according to the thickness of an adhesive layer and the amount of the active ingredient; FIG. 13 is a plan view showing a state in which a release paper is provided on a prefilled patch according to an embodiment of the present disclosure; FIG. 14 is a perspective view showing a state in which a handle is integrally connected with a capsule according to an embodiment of the present disclosure; FIG. 15 is a perspective view showing the handle shown in FIG. 14 being pulled in the direction of the arrow; FIG. 16 is a perspective view showing the handle shown in FIG. 14 completely separated from the capsule; and FIG. 17 is a perspective view showing a state in which the a release paper shown in FIG. 16 has been removed.

As shown in FIGS. 1, 2A and 2B, a prefilled patch 100 according to an embodiment of the present disclosure may include: an adhesive layer 110 configured to be attached to the skin, a capsule 120 which is provided on the adhesive layer 110 and in which an active ingredient or a drug is stored, and a handle 130 connected to a discharge hole 121 formed in the capsule 120.

The adhesive layer 110 may have a curvature around a peripheral portion thereof and may have various sizes and planar shapes so as to be attached to various parts of the body. In addition, the adhesive layer 110 may be made of a material that is harmless to the human body and has elasticity.

That is, since the user's skin to which the adhesive layer 110 is attached is not completely flat and has a curvature, it is preferable that the peripheral portion has a curved shape corresponding to this. The adhesive layer 110 attached to the skin with curvature receives pressure according to the user's movement, and the pressure may cause an active ingredient or a drug to be naturally discharged from the capsule 120 in which the active ingredient or the drug is stored onto the skin.

A known adhesive material may be coated or applied to a first side of the adhesive layer 110. For reference, the first side of the adhesive layer 110 is the part that is in direct contact with the skin, and a second side of the adhesive layer is the part that faces the outside.

Thus, the first side of the adhesive layer 110 may be attached to a release paper (not shown), but may be separated from the release paper and attached to the skin when used by a user.

The capsule 120 is disposed closer to the skin than the adhesive layer 110, and may be provided on the first side of the adhesive layer 110 in a pouch shape.

In addition, the capsule 120 provides an internal space where an active ingredient or a drug may be stored, and may have a planar area smaller than that of the adhesive layer 110.

For reference, the adhesive layer 110 and the capsule 120 may be made of a flexible thin film or polymer material, and are preferably made of a transparent material so that a user may visually check the inside.

As shown in FIGS. 3, 4A, 4B and 4C, the discharge hole 121 is formed in a localized area on one side of the capsule 120 facing the skin. The discharge hole 121 serves to discharge the active ingredient or the drug stored in the internal space of the capsule 120 toward the skin, and may be provided at least one in a localized area on one side of the capsule 120.

In an embodiment of the present disclosure, the drawing shows that discharge holes 121 are formed in a pair on one surface of the capsule 120 at a distance from each other.

In addition, as shown in FIGS. 4A, 4B and 4C, the discharge hole 121 may be formed in a circular, cross-shaped, straight, or circular shape, and may be blocked by the handle 130, which will be described later.

As shown in FIGS. 1 to 3, the handle 130 serves to block the discharge holes 121 formed in the capsule 120, and also serves to open the discharge holes 121 by being separated from one side of the capsule 120 by a user.

That is, one longitudinal end of the handle 130 is connected to the localized area on one side of the capsule 120, thereby blocking the discharge holes 121 formed in the capsule 120, and the other longitudinal end of the handle 130 may be exposed to the outside of the adhesive layer 110.

When the user pulls the other longitudinal end of the handle 130 exposed to the outside of the adhesive layer, one longitudinal end of the handle 130 may be separated from one side of the capsule 120 and come out of the adhesive layer 110. Then, the discharge holes 121 formed on one side of the capsule 120 are opened, and the active ingredient or the drug stored in the internal space of the capsule 120 may be discharged toward the skin.

The active ingredient or the drug released from the internal space of the capsule 120 may be absorbed into the skin as the active ingredient or the drug diffuses across the skin to which the adhesive layer 110 is attached.

For reference, active ingredients or drugs stored in the capsule 120 contain ingredients for the purpose of disease prevention and treatment, but is not limited thereto, and may be genetic materials, epidermal growth factor (EGF) or hyaluronic acid for skin care.

As shown in FIGS. 1 and 3, one end of the handle 130 may be branched into a number corresponding to the number of discharge holes 121. In an embodiment of the present disclosure, one end of the handle 130 is divided into two branches corresponding to the pair of discharge holes 121, and accordingly, the handle 130 is shown in the drawing as having an overall "Y" shape.

Meanwhile, the handle 130 has an adhesive strength that is relatively lower than that of the adhesive layer 110 and the capsule 120 so as to be easily separated from the capsule 120 when the user pulls the handle 130. In addition, one longitudinal end of the handle 130 is attached to one surface of the capsule 120 by adhesive or heat fusion method, and the tensile strength of the handle 130 is set to be greater than the adhesive strength developed around the discharge holes 121 to prevent a longitudinal portion of the handle 130 from breaking when the user pulls the handle 130. It is obvious that the tensile strength of the capsule 120 is greater than the adhesive strength between the handle 130 and the discharge holes.

Thus, as shown in FIGS. 2A and 2B, when the adhesive layer 110 is attached to the skin, the user may easily separate the handle 130 from the bottom of the capsule 120 by pulling the other longitudinal end of the handle 130 exposed to the outside of the adhesive layer 110.

In the above state, when the user attaches the adhesive layer 110 to the skin again, the active ingredient or the drug discharged from the capsule 120 may be absorbed into the skin without leaking out of the area confined by the adhesive layer 110.

In particular, as shown in FIG. 2B, when the adhesive layer 110 is attached to the curved skin, the internal pressure of the capsule 120 increases as the capsule 120 corresponds to the curved skin surface shape, and due to the internal pressure, the discharge holes 121 are opened and the stored drug or active ingredient may be easily delivered to the skin.

Therefore, in the prefilled patch 100 according to an embodiment of the present disclosure, since the adhesive layer 110 and the capsule 120 are deformed in response to the curved skin, the adhesive layer 110 and the capsule 120 maintain in close contact with the skin without flowing on the preset skin area. In addition, even if the user does not apply additional pressure to the capsule 120, the capsule 120 is provided with pressure on account of skin surface change due to body movements, so that the drug or active ingredient may be easily discharged onto the skin.

In addition, as shown in FIGS. 5 to 10, the prefilled patch 100 according to an embodiment of the present disclosure may further include: a microneedle 200 attached to the first side of the adhesive layer 110 with a planar area larger than that formed by the capsule 120 and smaller than the planar area formed by the adhesive layer 110.

The microneedle 200 may include: a substrate portion 210 attached to the adhesive layer 110; a plurality of carrying holes 220 formed in the substrate 210; and an insertion needle 230 provided to protrude from a portion of the substrate portion 210 that partitions the carrying holes 220 and configured to be inserted into the skin.

The substrate portion 210 may have the form of a thin plate having a predetermined area and thickness. As described above, the substrate portion 210 may be provided on the first side of the adhesive layer 110 coated or applied with an adhesive material. To be specific, as shown in FIG. 7, the substrate portion 210 may be disposed under the adhesive layer 110 and the capsule 120.

The substrate portion 210 may be manufactured in various sizes and shapes to correspond to the area of skin to which the substrate portion 210 is to be attached, and may be formed to have various curvatures so as to be in airtight contact with the curved skin. For reference, in an embodiment of the present disclosure, the substrate portion 210 is shown in the drawing as having the same shape as the adhesive layer 110.

The carrying hole 220 may be provided in the substrate portion 210 by a molding method using a press or a cutting device using a laser, and the plurality of carrying holes 220 may be provided at intervals on the surface of the substrate portion 210.

The carrying hole 220 may be provided in the substrate portion 110 in a circular or regular polygonal shape, and is preferably formed in a regular hexagonal shape in order to increase the structural durability of the substrate portion 110.

When the carrying hole 220 is provided in the shape of a regular hexagon, the substrate portion 210 may have a honeycomb structure.

The substrate portion 210 having a honeycomb structure may prevent portions of the substrate portion 210 disposed between the carrying holes 220 from being deformed or damaged by a pressing piece of a press when pressing with the press in order to vertically erect the insertion needle 230, which is placed in a lying state inside the carrying hole 220.

To be specific, in the process of inserting the pressing piece provided in a movable mold of the press into the carrying hole 220, the insertion needle 230 placed in a lying state is pressed and bent in the vertical direction, and at this time, there is a risk that the portions of the substrate portion 210 disposed between the carrying holes 220 may be affected by the pressing piece and be deformed or torn.

However, in the microneedle 200 according to an embodiment of the present disclosure, the carrying hole 220 is provided in the form of a regular hexagon so that the substrate portion 210 may be formed into a honeycomb structure, which increases the overall strength of the substrate portion 210 and prevents the substrate portion 210 from being deformed or damaged during the work process using a press.

The carrying hole 220 configured as above provides a space where the active ingredient or drug discharged through the discharge holes 121 of the capsule 120 may be stored. That is, the active ingredient or drug discharged through the discharge holes 121 may spread along the planar area of the substrate portion 210 and be stored in the carrying holes 220.

In addition, the carrying hole 220 is preferably formed at a position corresponding to the discharge hole 121 formed in the capsule 120. That is, it is preferable that the carrying holes 220 and the discharge holes 121 are formed at positions corresponding to each other so that the active ingredient or drug may be smoothly discharged and spread through the discharge holes 121 when the handle 130 is separated from one side of the capsule 120.

The carrying hole 220 also serves to enable the substrate portion 210 and the attached adhesive layer 110 to further adhere to the skin. In other words, portions of the adhesive layer 110 disposed at positions corresponding to the carrying holes 220 may be attached to the skin through the carrying holes 220.

When the substrate portion 210 comes into close contact with the skin, only the peripheral area of the adhesive layer 110 that is not in contact with the substrate portion 210 is attached to the skin, and thus the substrate portion 210 may flow on the skin. However, since the plurality of carrying holes 220 are formed in the substrate portion 210, the adhesive surface of the adhesive layer 110 may be attached to the skin by passing through the carrying holes 220. Accordingly, even if the user moves his or her body, the substrate portion 210 may be fixedly placed at the initial attachment spot.

Meanwhile, as shown in FIG. 7, since the substrate portion 210 comes into close contact with the skin when the adhesive layer 110 is attached to the skin, it is preferable that the substrate portion 210 does not interfere with the movement of the handle 130 during the process of separating the handle 130.

Thus, as shown in FIG. 8, the substrate portion 210 is preferably provided with a guide area 240 corresponding to the shape of the handle 130.

The guide area 240 provides a movement path for the handle 130 so that the substrate portion 210 does not interfere with the movement of the handle 130 when one longitudinal end of the handle 130 connected to the capsule 120 is separated from the capsule 120. Thus, when the user pulls the handle 130 to discharge the active ingredient or drug stored in the capsule 120, the handle 130 moves along the guide area 240 provided on the substrate portion 210, and thus the handle 130 is easily moved without being hindered by the substrate portion 210 and may be easily separated from the capsule 120.

When the carrying hole 220 is formed in the shape of a regular polygon, as shown in FIG. 10, the insertion needle 230 may be provided at the center of the inner edge of the substrate portion 210 partitioning the carrying holes 220.

If the insertion needle 230 is provided at the inner vertex of the substrate portion 210 partitioning the carrying holes 220, there is a risk that the insertion needle 230 may break during the process (pressure processing using a press) of bending the insertion needle 230, which was lying horizontally. Thus, in order to prevent the insertion needle 230 from breaking, it is preferable to provide the insertion needle 230 at the center of the inner edge of the substrate portion 210 that partitions the carrying holes 220.

The insertion needle 230 allows the active ingredient or drug stored in the carrying hole 220, or the active ingredient or drug delivered to the surface of the substrate portion 210, to penetrate into the skin.

As shown in FIG. 7, when the adhesive layer 110 is attached to the skin, a plurality of insertion needles 230 are inserted into the skin, and during this process, the active ingredient or drug stored in the capsule 120 may be delivered to the deeper layers of the skin through the plurality of insertion needles 230.

In an embodiment of the present disclosure, because the insertion needles 230 are arranged in a predetermined pattern based on the carrying holes 220, the active ingredient or drug discharged through the discharge holes 121 may be uniformly delivered to the deeper layers of the skin via the insertion needles 230.

In addition, as shown in FIGS. 9 to 11, the microneedle 200 according to an embodiment of the present disclosure may further include: a carrying groove 231 that provides a path through which the active ingredient or drug discharged through the discharge holes 121 may flow.

The carrying groove 231 extends from a portion of the area defined by the substrate portion 210 toward the end of the insertion needle 230, and may be formed in the substrate portion 210 and the insertion needle 230 to have a predetermined depth.

The portion of the carrying groove 231 formed in the substrate portion 210 serves to deliver the active ingredient or drug diffused to the surface of the substrate portion 210 to the insertion needle 230.

That is, when the discharge holes 121 of the capsule 120 are opened, the active ingredient stored in the capsule 120 diffuses into the flat area formed by the substrate portion 210. At this time, the diffused active ingredient or drug flows in the direction in which the carrying hole 220 is formed and is stored in the carrying hole 220, or stays in the surface area of the substrate portion 210 where the carrying hole 220 is not provided.

In this case, as shown in FIG. 11, the portion of the carrying groove 231 formed in the substrate portion 210 serves to deliver the active ingredient or drug remaining in the surface area of the carrying hole 220 to the insertion needle 230.

On the other hand, the portion of the carrying groove 231 formed in the insertion needle 230, as shown in FIG. 11, serves to deliver the active ingredient or drug stored in the carrying hole 220 into the skin, and serves to receive the active ingredient or drug delivered from the portion of the carrying groove 231 formed on the substrate portion 210 and deliver the received active ingredient or drug into the skin.

That is, when the insertion needle 230 is inserted into the skin, a gap is not created between the insertion needle 230 and the deeper layers of the skin due to the contractile force of the skin, making it difficult for an active ingredient or a drug to penetrate. The carrying groove 231 according to an embodiment of the present disclosure is a component prepared in consideration of the contractile force of the skin, and allows the active ingredient or drug discharged from the capsule 120 to flow to the insertion needle 230 already inserted in the hypodermis, making it easy to deliver the active ingredient or drug to the deeper layers of the skin.

The carrying groove 231 is preferably formed on both one side and the other side of the substrate portion 210 and the insertion needle 230.

This is because, in order to efficiently deliver the active ingredient or drug remaining on one side and the other side of the substrate portion 210 and the active ingredient or drug stored in the carrying hole 220 to the deeper layers of the skin, it is more efficient to form the carrying groove 231 on both surfaces of the substrate portion 210 and the insertion needle 230 rather than forming the carrying groove 231 on one surface of the substrate portion 210 and the insertion needle 230.

For example, if the carrying groove 231 is formed only on the other surface of the substrate portion 210 and the other surface of the insertion needle 230, a path through which the remaining on one side of the active ingredient or drug remaining substrate portion 210 may flow is not provided, so that the active ingredient or drug remaining on one side of the substrate portion 210 continues to remain on one side of the substrate portion 210, ultimately preventing the active ingredient or drug remaining on one side of the substrate portion 210 from being absorbed through the skin or penetrating deeper into the skin.

In addition, since the active ingredient or drug is not delivered at all to the deep skin area facing one side of the insertion needle 230, the effect of the active ingredient or drug is reduced. At this time, one side of the substrate portion 210 is the side that faces the skin and is in direct contact with the skin.

Thus, in order to easily deliver the active ingredient or drug that flows and stays on one side of the substrate portion 210 into the deeper layers of the skin, it is preferable to form the carrying groove 231 on both one side and the other side of the substrate portion 210 and the insertion needle 230 as shown in FIG. 11. In that case, the active ingredient or drug flows in the direction of arrow A and arrow B shown in FIG. 11, and may be effectively delivered to the deep skin area facing one side of the insertion needle 230 and to the deep skin area facing the other side of the insertion needle 230.

As shown in FIGS. 9 to 11, the microneedle 200 according to an embodiment of the present disclosure may further include: a slit groove 232 that guides the active ingredient or drug loaded in the carrying groove 231 to the end of the insertion needle 230.

As mentioned above, the slit groove 232 allows the active ingredient or drug stored in the carrying groove 231 to easily flow into the deeper layers of the skin via the tip of the insertion needle 230.

As shown in FIG. 11, the slit groove 232 allows the active ingredient or drug to be discharged through the end of the insertion needle 230, and one longitudinal end of the slit groove 232 may be connected in communication with the carrying groove 231 formed on the insertion needle 230, and the other longitudinal end of the slit groove 232 may be connected to the end of the insertion needle 230.

Accordingly, the active ingredient or drug flowing into the carrying groove 231 may be discharged to the end of the insertion needle 230 via the slit groove 232.

In other words, while the carrying groove 231 formed on both one side and the other side of the insertion needle 230 delivers the active ingredient or drug to the deep skin areas facing one side and the other side of the insertion needle 230, the slit groove 232 serves to deliver the active ingredient or drug flowing into the slit groove 232 to the deep skin area facing the tip of the insertion needle 230.

Thus, the active ingredient or drug may be delivered evenly into the deeper layers of the skin by the carrying groove 231 and the slit groove 232.

For reference, the carrying hole 220, the insertion needle 230, the carrying groove 231, and the slit groove 232 provided in the substrate portion 210 may be formed on the substrate portion 210 by a known lithography or etching technique.

In addition, the substrate portion 210 and the insertion needle 230 may be made of a metal containing at least one of magnesium, calcium, zinc, iron, and which are used as bioresorbable metals.

For reference, as for the bioresorbable metals, magnesium-based alloys have been produced and commercialized domestically and internationally for application as orthopedic implants. Bioresorbable metals applied to orthopedic implants focuses on reducing the rate of decomposition in the body as much as possible or improving corrosion resistance for safe fracture fixation.

However, unlike the bioresorbable metals used in orthopedics, the bioresorbable metal used as the material for the microneedle 200 according to an embodiment of the present disclosure may accelerate the decomposition rate in the body, allowing the release of drugs and supply of minerals into the deeper layers of the skin.

For example, magnesium, calcium, and zinc, which are used as bioresorbable metals, may have a mechanism for decomposing by reaching with water in the body and releasing hydrogen gas.

The substrate portion 210 and the insertion needle 230 made of the bioresorbable metals as described above emit ions and release decomposition products into the deeper layers of the skin, and the hydrogen gas generated as a by-product provides a swelling effect in the deeper layers of the skin, which may also lead to wrinkle improvement effect.

In addition, ZnO and MgCl, which are by-products produced when magnesium and zinc, which are components of bioresorbable metals, are inserted into the body, remain in the deeper layers of the skin and may serve as an enhancer for drug delivery to improve the absorption of active ingredients or drugs carried in the substrate portion 210 and the insertion needle 230 into the deeper layers of the skin. Accordingly, the substrate portion 210 and the insertion needle 230 made of the bioresorbable metals may effectively deliver drugs loaded therein to the deeper layers of the skin.

For reference, in FIG. 12, a test result table is shown to check whether an active ingredient is delivered to the skin and whether the active ingredient leaks depending on the thickness of the adhesive layer 110 and the amount of the active ingredient stored in the capsule 120.

As shown in FIG. 12, it is possible to check whether an active ingredient stored in the capsule 120 is delivered to the skin and whether the active ingredient leaks when the thickness of the adhesive layer is set to 0.5 mm, 1 mm, 2 mm, and the amount of the active ingredient stored in the capsule 120 is set to 0.01 ml/cm$^2$, 0.005 ml/cm$^2$, 0.01 ml/cm$^2$, 1 ml/cm$^2$, 3 ml/cm$^2$.

As shown in sample 1 of the test result table, when the thickness of the adhesive layer 110 is 0.5 mm, and the amount of the active ingredient stored in the capsule 120 is 0.01 ml/cm$^2$, it was found that the active ingredient was discharged from the capsule 120 onto the skin. However, the active ingredient discharged from the capsule 120 leaked to the outside of the adhesive layer 110.

As shown in sample 2 of the test result table, when the thickness of the adhesive layer 110 is 1 mm, and the amount of the active ingredient stored in the capsule 120 is 0.005 ml/cm$^2$, it was found that the active ingredient was not discharged from the capsule 120 onto the skin.

As shown in sample 3 of the test result table, when the thickness of the adhesive layer 110 is 1 mm, and the amount of the active ingredient stored in the capsule 120 is 0.01 ml/cm$^2$, it was found that the active ingredient was discharged from the capsule 120 onto the skin. It was also found that the active ingredient discharged from the capsule 120 did not leak to the outside of the adhesive layer 110.

As shown in sample 4 of the test result table, when the thickness of the adhesive layer 110 is 1 mm, and the amount of the active ingredient stored in the capsule 120 is 1 ml/cm$^2$, it was found that the active ingredient was discharged from the capsule 120 onto the skin. It was also found that the active ingredient discharged from the capsule 120 did not leak to the outside of the adhesive layer 110.

As shown in sample 5 of the test result table, when the thickness of the adhesive layer 110 is 1 mm, and the amount of the active ingredient stored in the capsule 120 is 3 ml/cm$^2$, it was found that the active ingredient was discharged from the capsule 120 onto the skin. However, the active ingredient discharged from the capsule 120 leaked to the outside of the adhesive layer 110.

As shown in sample 6 of the test result table, when the thickness of the adhesive layer 110 is 2 mm, and the amount of the active ingredient stored in the capsule 120 is 1 ml/cm$^2$, it was found that the active ingredient was discharged from the capsule 120 onto the skin. It was also found that the active ingredient discharged from the capsule 120 did not leak to the outside of the adhesive layer 110.

As shown in sample 7 of the test result table, when the thickness of the adhesive layer 110 is 2 mm, and the amount of the active ingredient stored in the capsule 120 is 3 ml/cm$^2$, it was found that the active ingredient was discharged from the capsule 120 onto the skin. However, the active ingredient discharged from the capsule 120 leaked to the outside of the adhesive layer 110.

As can be seen in the test result table, as the thickness of the adhesive layer 110 decreases, the adhesion to the skin decreases and a gap is formed through which the active ingredient can leak, and thus the active ingredient discharged from the capsule 120 leaks to the outside of the adhesive layer 110.

In addition, the larger the amount of the active ingredient stored in the capsule 120, the more the active ingredient discharged from the capsule 120 leaked to the outside of the adhesive layer 110.

Thus, it is desirable to optimally set the thickness of the adhesive layer 110 and the amount of the active ingredient stored in the capsule 120. More preferably, when the thickness of the adhesive layer 110 is set to 1 mm~2 mm, and the amount of the active ingredient stored in the capsule 120 is set to 0.01 ml/cm$^2$~2 ml/cm$^2$, the active ingredient stored in the capsule 120 is easily delivered to the skin and may also prevent leakage to the outside.

In addition, as shown in FIG. 13, the prefilled patch 100 according to an embodiment of the present disclosure may further include: a pair of release papers 141 and 142.

The release papers 141 and 142 may be attached to the peripheral area of the adhesive layer 110 that is not in contact with the substrate portion 210, and may be separated from the adhesive layer 110 based on a fold line L.

For example, one side release paper 141 may be separated from the adhesive layer 110 in the direction of arrow A based on the fold line L, while the other side release paper 142 may be separated from the adhesive layer 110 in the direction of arrow B based on the fold line L.

Meanwhile, the other side release paper 142 may be connected to the handle 130. The other side release paper 142 may be attached to the peripheral area of the adhesive layer 110 with an area including the handle 130 that blocks the discharge holes 121 formed in the capsule 120. In this case, the other side release paper 142 may be attached to one end and the other end of the handle 130 in the longitudinal direction.

That is, the other side release paper 142 may be attached to the longitudinal end portion of the handle 130 that does not overlap the capsule 120.

Thus, when the user separates the other side release paper 142 from the adhesive layer 110 in the direction of arrow B, the handle 130 may be separated from the adhesive layer 110 together with the other side release paper 142. Then, the discharged holes 121 of the capsule 120 are opened and the active ingredient or drug stored in the capsule 120 is delivered to the skin.

Hereinafter, a method of manufacturing a prefilled patch according to an embodiment of the present disclosure will be described.

The method of manufacturing a prefilled patch according to an embodiment of the present disclosure may include: a first step of perforating a discharge hole 121 in a capsule 120; a second step of joining a handle 130 to the discharge hole 121 formed in the first step; a third step of filling the capsule 120 provided in the first step with a drug or an active ingredient and sealing the capsule 120; fourth step of attaching release papers 141 and 142 to a peripheral area of an adhesive layer 110; a fifth step of attaching the capsule 120 sealed in the third step to a central area of the adhesive layer 110 that is not directly attached to the release papers 141 and 142 in the fourth step; and a sixth step of attaching a substrate portion 210 of a microneedle 200 to the adhesive layer 110 completed up to the fifth step.

First, in the first step, the discharge hole 121 is formed in either a first film or a second film constituting the capsule 120. The first film and the second film are components that provide a space where a drug or an active ingredient may be accommodated, and are sealed in the third step, which will be described later. For reference, various known drilling methods may be used to form a hole in the capsule 120 to provide the discharge hole 121.

In the second step, the longitudinal end of the handle 130 may be bonded to the film portion of the capsule 120 where the discharge hole 121 is formed.

In the third step, a drug or an active ingredient may be filled into the internal space formed by the first film and the second film of the capsule 120. At this time, it is desirable that one sides of the first film and the second film are already sealed. Once the drug or active ingredient is filled, the other sides of the first film and the second film are finally sealed to achieve a sealed state.

In the fourth step, the adhesive layer 110 and the release papers 141 and 142 are combined. To be specific, the release papers 141 and 142 are attached to a border area on one side of the total area defined by the adhesive layer 110. In fact, since the border area of the adhesive layer 110 is a part that is in direct contact with the skin without being interfered with by other components, it is preferable that the release papers 141 and 142 are attached to maintain the adhesion of the area.

In the fifth step, the capsule 120 to which the handle 130 is connected may be attached to the central portion of the adhesive layer 110 that is not attached to the release papers 141 and 142. In this case, the film of the capsule 120 without the discharge hole 121 is disposed to face an adhesive surface of the adhesive layer 110 and attached to the adhesive surface, while the film of the capsule 120 in which the discharge hole 121 is formed and the handle 130 are located on the opposite side.

The sixth step is an optional process that attaches the above-described microneedle 200 to the adhesive surface of the adhesive layer 110. That is, the sixth step may be performed to implement the original function of the microneedle 200 and the deep skin delivery effect of the drug or active ingredient stored in the capsule 120.

The prefilled patch manufactured in the sixth step may be finally packaged and shipped.

So far, although specific embodiments according to the present disclosure have been described, various modifications are possible without departing from the scope of the present disclosure.

For example, in the internal space of the capsule 120, an ingredient that changes the color of the substrate portion 210 or an insertion needle 230 by reacting with the microneedle 200 made of bioresorbable metals may be stored.

Thus, the prefilled patch of the present disclosure may be used to check the user's physical condition on the basis of the degree to which the microneedle 200 is discolored, or may also be used as a patch to diagnose the presence or absence of a variety of viruses or disease infections using reagents.

In addition, as shown in FIGS. 14 to 17, the handle 130 may be integrally connected to the capsule 120. For reference, FIG. 14 shows a portion of one side of the prefilled patch 100 facing the user's skin.

As shown in FIG. 14, one longitudinal end of the handle 130 may be integrally connected to the capsule 120.

In addition, as shown in FIGS. 15 and 16, when the other longitudinal end of the handle 130 exposed to the outside of the adhesive layer 110 is pulled by the user and separated from the capsule 120, the portion of the capsule 120 that is integrally connected with one longitudinal end of the handle 130 may be cut.

As shown in FIGS. 16 and 17, since the cut portion of the capsule 120 created when the handle 130 is separated serves as a discharge hole for discharging the active ingredient or drug, there is no need to form a separate discharge hole in the capsule 120. In addition, since the handle 130 is provided in the process of manufacturing the capsule 120, the process of separately manufacturing the handle 130 and then joining the handle 130 to the capsule 120 may be omitted.

Meanwhile, when the handle 130 is pulled by the user, it is preferable that one end thereof in the longitudinal direction is easily torn from the capsule 120. Thus, the portion of the capsule 120 directly connected to one longitudinal end of the handle 130 may have relatively lower intensity than the rest of the capsule 120.

Alternatively, on the portion of the capsule 120 directly connected to one longitudinal end of the handle 130, a cutting line or perforated line may be provided. Accordingly, when the user pulls the other longitudinal end of the handle 130, one longitudinal end of the handle 130 may be easily torn off the capsule 120 due to the cutting line or perforated line.

For reference, the cutting line or perforated line may be provided as a groove formed along the separation direction of the handle 130 on the portion of the capsule 120 directly connected to one longitudinal end of the handle 130. The groove may be provided as a single groove or multiple grooves at the connection portion of the handle 130 and the capsule 120.

In addition, the groove forming the cutting line or perforated line may be provided by a known half-cut process using a laser or a blade forming process.

Therefore, the scope of the present disclosure should not be limited to the described embodiments, but should be determined by the scope of the patent claims described below as well as equivalents to the claims.

INDUSTRIAL APPLICABILITY

The present disclosure may be sold and used in various industrial fields such as the medical field and skin care field.

The invention claimed is:

1. A prefilled patch comprising:

an adhesive layer configured to be attached to skin;

a capsule which is provided on the adhesive layer and in which an active ingredient or a drug is stored; and a handle connected to a discharge hole formed in the capsule, wherein the handle is separated from the capsule by a user to open the discharge hole, the discharge hole is formed in a localized area on one side of the capsule, and one longitudinal end of the handle is connected to the localized area on one side of the capsule, thereby blocking the discharge hole.

2. The prefilled patch of claim 1, wherein the capsule is provided on a surface of the adhesive layer while being disposed closer to the skin than the adhesive layer, and has a planar area smaller than a planar area formed by the adhesive layer.

3. The prefilled patch of claim 1, wherein a first longitudinal end of the handle blocks the discharge hole formed in the capsule, and a second longitudinal end of the handle is exposed to outside of the adhesive layer.

4. The prefilled patch of claim 3, wherein the discharge hole is provided in plural numbers, and the first end of the handle is branched into a number corresponding to the number of the discharge hole.

5. The prefilled patch of claim 2, further comprising:

a microneedle provided by being attached to the adhesive layer with a planar area that is larger than the planar area formed by the capsule and smaller than the planar area formed by the adhesive layer.

6. The prefilled patch of claim 5, wherein the microneedle comprises:

a substrate portion configured to be attached to the adhesive layer;

a plurality of carrying holes formed in the substrate portion; and an insertion needle provided to protrude from a portion of the substrate portion that partitions the carrying holes, and configured to be inserted into the skin.

7. The prefilled patch of claim 6, wherein the discharge hole formed in the capsule corresponds to any one of the carrying holes.

8. The prefilled patch of claim 5, wherein the substrate portion is provided with a guide area that guides a movement of the handle so that the movement is not interfered with when a portion of the handle connected to the capsule is separated from the capsule.

9. The prefilled patch of claim 6, wherein the microneedle further comprises:

a carrying groove that provides a path for the active ingredient or the drug discharged through the discharge hole to flow, wherein the carrying groove is formed extending from a portion of the area formed by the substrate portion toward an end of the insertion needle.

10. The prefilled patch of claim 9, wherein the microneedle further comprises:

a slit groove that guides the active ingredient or the drug loaded in the carrying groove to the end of the insertion needle.

11. The prefilled patch of claim 6, wherein the substrate portion and the insertion needle of the microneedle are made of a bioresorbable metal, and the bioresorbable metal contains at least one of magnesium, calcium, zinc, and iron.

12. The prefilled patch of claim 1, further comprising:

a release paper attached to a peripheral area of the adhesive layer.

13. The prefilled patch of claim 12, wherein the release paper is provided as a pair and is attached to the peripheral area of the adhesive layer, wherein one and the other of the pair of the release papers are moved in different directions to be separated from the adhesive layer, and one of the release papers is attached to the handle.

* * * * *